(12) United States Patent
Hetzer et al.

(10) Patent No.: US 7,779,838 B2
(45) Date of Patent: Aug. 24, 2010

(54) INHALATION THERAPY DEVICE

(75) Inventors: Uwe Hetzer, Munich (DE); Thomas Gallem, Munich (DE); Robert Waldner, Peiting (DE)

(73) Assignee: PARI Pharma GmbH, Starnberg (DE)

( * ) Notice: Subject to any disclaimer, the term of this patent is extended or adjusted under 35 U.S.C. 154(b) by 1097 days.

(21) Appl. No.: 11/474,137

(22) Filed: Jun. 23, 2006

(65) Prior Publication Data

US 2006/0289002 A1 Dec. 28, 2006

(30) Foreign Application Priority Data

Jun. 24, 2005 (DE) .................. 10 2005 029 498

(51) Int. Cl.
*A61M 11/00* (2006.01)
(52) U.S. Cl. .................. 128/203.16; 128/203.14
(58) Field of Classification Search .................. 128/203.12–203.15, 203.16, 203.19, 203.21, 128/203.23–203.27, 200.11–200.22
See application file for complete search history.

(56) References Cited

U.S. PATENT DOCUMENTS

| | | | |
|---|---|---|---|
| 4,462,397 A | 7/1984 | Suzuki | |
| 4,951,661 A | 8/1990 | Sladek | |
| 5,586,550 A * | 12/1996 | Ivri et al. | 128/200.16 |
| 5,758,637 A * | 6/1998 | Ivri et al. | 128/200.16 |
| 6,014,972 A * | 1/2000 | Sladek | 128/203.12 |
| 6,062,214 A * | 5/2000 | Howlett | 128/200.23 |
| 6,085,740 A * | 7/2000 | Ivri et al. | 128/200.16 |
| 6,363,932 B1 * | 4/2002 | Forchione et al. | 128/203.12 |
| 6,390,090 B1 * | 5/2002 | Piper | 128/203.28 |
| 6,412,481 B1 | 7/2002 | Bienvenu et al. | |
| 6,962,151 B1 * | 11/2005 | Knoch et al. | 128/200.14 |
| 7,059,320 B2 * | 6/2006 | Feiner et al. | 128/200.16 |
| 7,204,245 B2 * | 4/2007 | Johnson et al. | 128/200.14 |
| 2003/0072717 A1 | 4/2003 | Reinhold et al. | |
| 2006/0054166 A1 * | 3/2006 | Knoch et al. | 128/200.14 |
| 2006/0118106 A1 * | 6/2006 | Schuckmann | 128/200.14 |
| 2008/0299049 A1 * | 12/2008 | Stangl | 424/45 |

FOREIGN PATENT DOCUMENTS

DE 20100648 U1 5/2001
DE 103 20 143 A1 12/2004

OTHER PUBLICATIONS

Search Report dated Sep. 29, 2006 from corresponding European Appln. No. 06010290.2.

* cited by examiner

*Primary Examiner*—Steven O Douglas
(74) *Attorney, Agent, or Firm*—Wolf, Greenfield & Sacks, P.C.

(57) ABSTRACT

An inhalation therapy device includes a supply element for a gaseous medium, for example ventilation air of a ventilation device, and a flow influencing element, by means of which a sheath flow is formed around an expansion area for an aerosol generated by an aerosol generator for therapeutic administration. Deposition of aerosol droplets or particles on the inner way of the housing of the inhalation therapy device is effectively prevented in this manner.

11 Claims, 2 Drawing Sheets

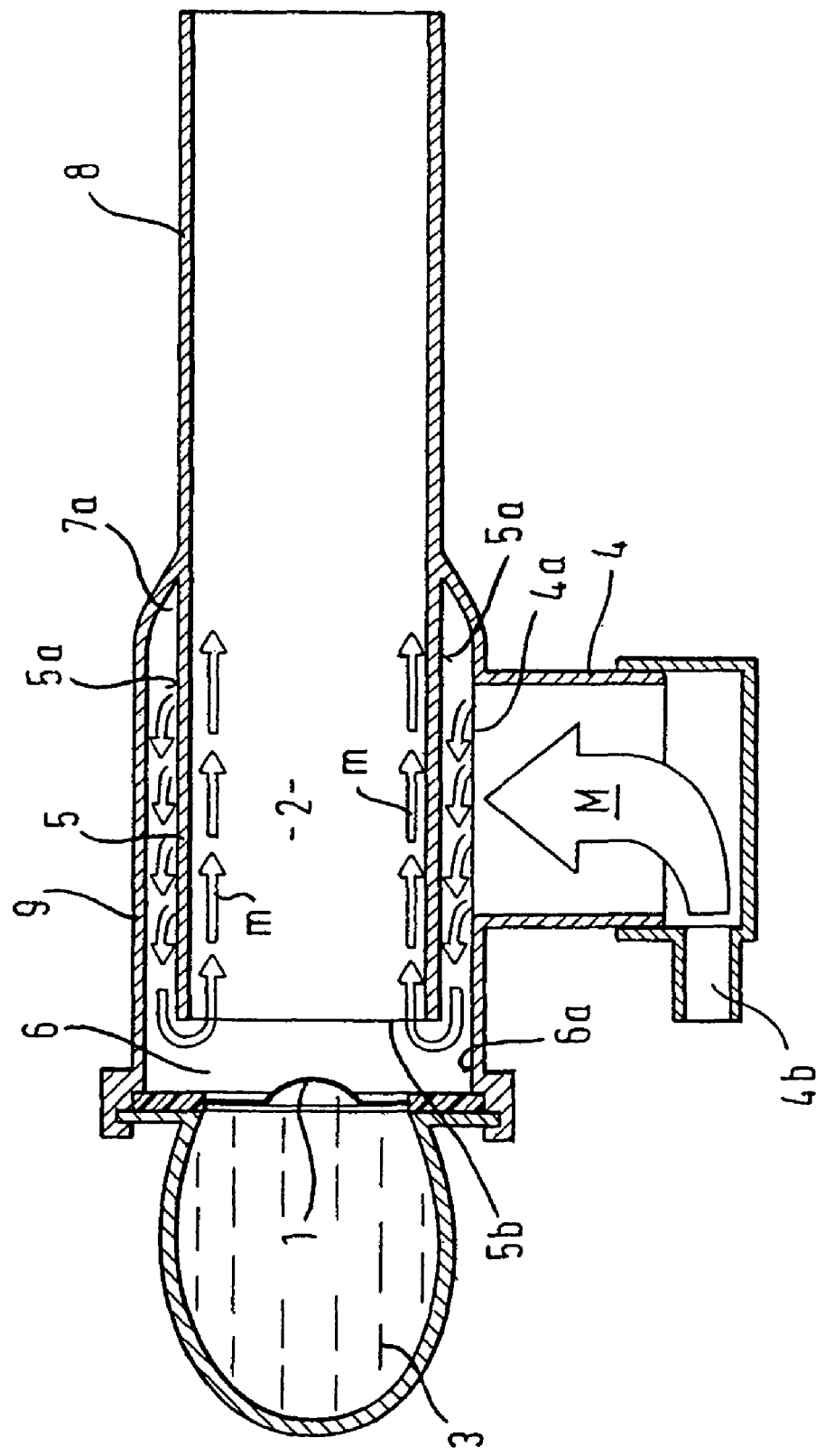

INHALATION THERAPY DEVICE

FIELD OF THE INVENTION

The present invention relates to inhalation therapy devices, by means of which a medicament is provided to a patient in the form of an aerosol to be inhaled.

BACKGROUND OF THE INVENTION

Aerosols for therapeutic purposes, which have to satisfy high requirements, are generated with inhalation therapy devices. The requirements arise from the therapy to be carried out with the inhalation therapy device. The core piece of an inhalation therapy device is the aerosol generator, which, when actuated by a control unit for aerosol generation provided in the inhalation therapy device, generates an aerosol from a medicament that is often in the form of a liquid formulation or another fluid. In an advantageous embodiment, the aerosol generator comprises at least one membrane and an oscillation generator, the membrane being caused to oscillate by the oscillation generator and then generating an aerosol from the medicament supplied on the one side of the membrane, which is released on the other side of the membrane. The resulting aerosol cloud expands in a spatial area located in front of the aerosol generator, which is often realised as a chamber in the housing of the inhalation therapy device. In order to minimise medicament loss, the shape and size of the chamber are advantageously configured such that as few aerosol droplets/particles as possible become deposited on the wall of the chamber.

The use of inhalation therapy devices in connection with ventilation devices by means of which a patient is ventilated or receives a breathing pattern predetermined by the supplied ventilation air is problematic since the carefully coordinated generation and expansion of the aerosol cloud must be harmonised with the introduction of the aerosol into the ventilation air.

A connection device for this purpose is known from U.S. Pat. No. 4,951,661, which comprises a T-shaped tube member that is inserted into the ventilation air hose of a ventilation device that leads to the patient. An aerosol generator is provided on the tube piece which discharges in a vertical direction into the tube piece that can be inserted into the respiratory air hose, said aerosol generator generating an aerosol cloud which enters the ventilation air via the discharging tube piece. The design of the T-piece is not optimal in terms of flow technology, which leads to considerable aerosol loss, and thus to losses in medicament. DE 103 20 143 A also proposes T-shaped connections to a ventilation hose, via which an aerosol provided by an aerosol generator is introduced into the ventilation hose. The T-pieces known from DE 103 20 143 A are, however, designed in a considerably more effective manner as regards flow technology since virtually the entire cross-section of the tube piece discharging into the ventilation hose is available for supply of the aerosol.

Aerosol losses nevertheless occur time and again in connection with the known T-pieces for connecting an inhalation therapy device to a ventilation air hose of a ventilation device owing to the deposition of aerosol droplets/particles on various surfaces.

SUMMARY OF THE INVENTION

In view of the above, the object to be solved by the present invention is to provide an inhalation therapy device in which the generated aerosol and a gaseous medium, in particular air, are brought together and offered to a patient for inhalation in an advantageous manner.

A further object of the present invention is to provide an inhalation therapy device which is particularly suitable for use in connection with a ventilation device.

These and further objects will be solved by an inhalation therapy device comprising: an aerosol generating device, designed to generate an aerosol from a liquid containing a medicament and to release said aerosol into an expansion spatial area, a liquid storage apparatus, designed to store said liquid and to supply the liquid to said aerosol generating device, a supply means, designed to supply a gaseous medium, in particular air, and a flow influencing means, designed to influence the flow of the supplied gaseous medium in such a manner that the gaseous medium forms a sheath flow around the expansion spatial area for the aerosol.

These and further objects will also be solved by an inhalation therapy device comprising an aerosol generating device, designed to generate an aerosol from a liquid containing a medicament and to release said aerosol into an expansion spatial area, a liquid storage apparatus, designed to store said liquid and to supply the liquid to said aerosol generating device, a supply means, designed to supply a gaseous medium, in particular air, and a cylindrical tube piece arranged around the expansion spatial area such that the supplied gaseous medium impinges upon the outer sheath surface of the tube piece and flows to a front end in the interior of the tube piece.

According thereto, in a preferred embodiment, an inhalation therapy device according to the invention comprises an aerosol generating device, which is designed to generate an aerosol from a liquid containing a medicament and to release the aerosol into an expansion spatial area, a liquid storage apparatus, which is designed to store the liquid and to supply the liquid to the aerosol generating device, a supply means designed to supply a gaseous medium, in particular air, and a cylindrical tube piece arranged around the expansion spatial area such that the supplied gaseous medium impinges upon the outer sheath surface of the tube piece and flows to a front end in the interior of the tube piece.

A deflection and redirection of the flow of the supplied gaseous medium can be achieved in an effective manner by means of the tube piece. The gaseous medium enters the area in which the aerosol cloud, generated by the aerosol generator from the stored liquid, expands via the rim of the front end.

In a generalised approach, an inhalation therapy device according to the invention comprises, in addition to the aforementioned aerosol generating device, liquid storage apparatus and supply means, a flow influencing means, which is designed to influence the flow of the supplied gaseous medium in such a manner that the gaseous medium forms a sheath flow around the expansion spatial area for the aerosol.

The sheath flow is thereby to be understood as a quasi-laminar flow of the gaseous medium in the regions at the rim of the expansion spatial area for the aerosol cloud.

BRIEF DESCRIPTION OF THE DRAWINGS

The invention will be described in more detail below by means of embodiments and with reference to the enclosed drawings.

In the drawings:

FIG. 2 shows a cut top view of the first embodiment of an inhalation therapy device according to the invention.

DETAILED DESCRIPTION

Figure 1:
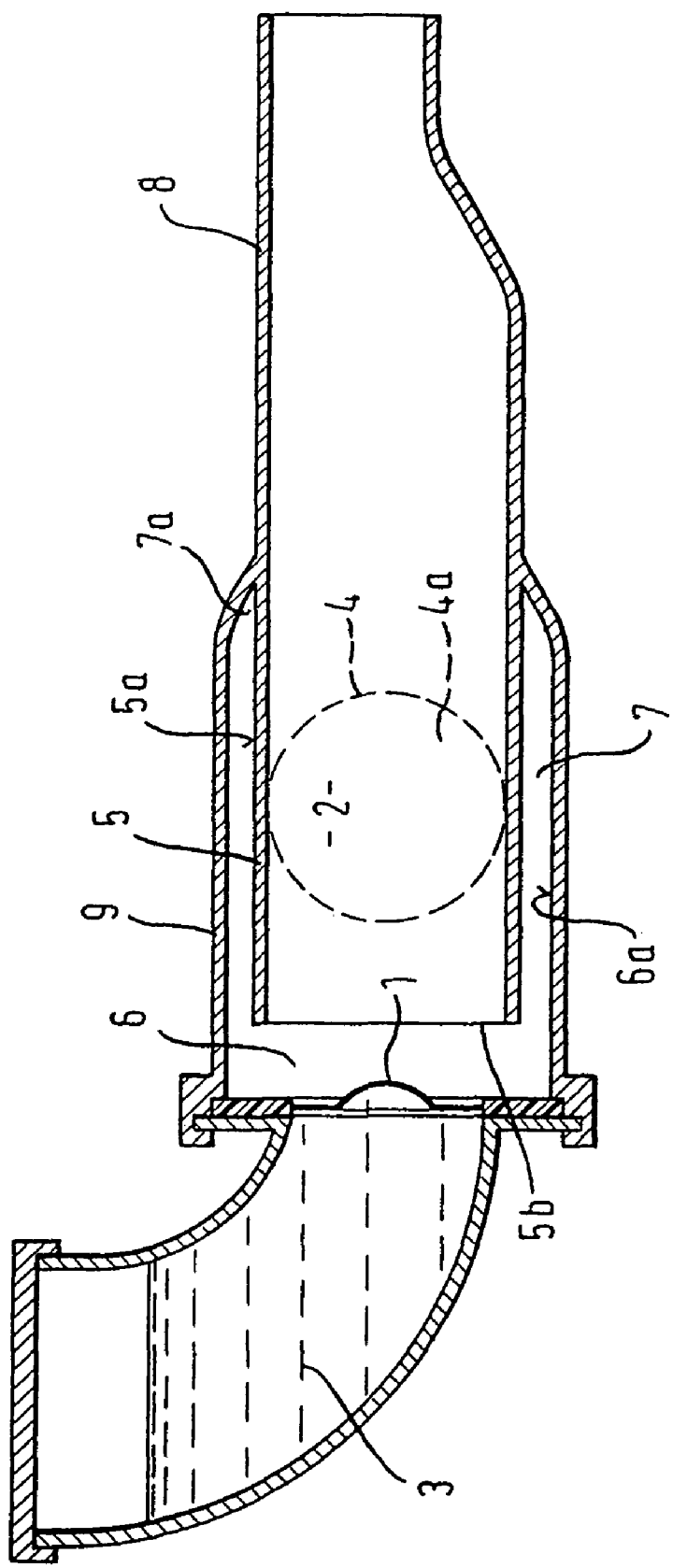
FIG. 1 shows a cut side view of a first embodiment of an inhalation therapy device according to the invention.

In the following, an embodiment of an inhalation therapy device according to the invention will be explained by means of FIGS. 1 and 2, which both show the first embodiment in a cut view, however from different angles.

Shown in FIGS. 1 and 2 is an inhalation therapy device according to the invention, which comprises an aerosol generating device 1, for example a membrane aerosol generator. The aerosol generating device 1 generates an aerosol from a medicament-containing liquid or fluid, which it releases into an expansion spatial area 2 in which the generated aerosol can expand. In particular in membrane aerosol generators, generation and release of the aerosol occurs in the form of an aerosol cloud expanding to a certain extent in a specific direction, which expands from the aerosol generator 1 into the expansion area 2.

The liquid to be nebulised is stored in a liquid storage apparatus 3, for example a liquid reservoir, and is supplied to the aerosol generating device 1. It is noted at this point that differing from the embodiment of an inhalation therapy device according to the invention as shown in FIGS. 1 and 2, storage and supply of the liquid to be nebulised can also be carried out by separate devices; the liquid storage apparatus 3 shown in FIGS. 1 and 2, which simultaneously serves storage and supply of the liquid, is, however, preferred.

The embodiment of an inhalation therapy device according to the invention furthermore comprises a supply means 4 for supplying a gaseous medium, in particular air, a therapeutically effective gas or a gas suitable for diagnosis. The gaseous medium is supplied to the inhalation therapy device according to the invention via the supply means 4 so that it can be inhaled by a patient during the inhalation therapy. In a particularly preferred design of the first embodiment, the supply means 4 is suitable for supplying the ventilation air of a ventilation device (not shown), which will not be explained in more detail at this point, but which is basically known to the person skilled in the art active in this field. However, it must be taken into consideration for the interpretation of the supply means 4 of the invention in this particular design that the supply means 4 is thereby preferably designed to supply all of the respiratory air so that the air required for respiration can be supplied to the patient via the supplied ventilation air by means of the supply means 4 of the inhalation therapy device according to the invention. It is possible in this manner, by means of an inhalation therapy device of the invention according to the first embodiment, to ventilate the patient or to give the patient a predetermined breathing pattern since all of the air provided for respiration is supplied via the supply means 4. If ventilation air is not being supplied by a ventilation device via the supply means 4, the supply means 4 can be designed to supply ambient air, for example by opening in the direction of the surrounding environment. The active supply of the gaseous medium via the supply means 4 as described above with regard to the ventilation device is, however, the preferred embodiment of the invention.

In the embodiment of an inhalation therapy device according to the present invention as shown in FIGS. 1 and 2, the gaseous medium supplied via the supply means 4 impinges upon a flow influencing means 5. The flow of the supplied gaseous medium M is influenced by the flow influencing means 5 in such a manner that the gaseous medium M forms a sheath flow m around the expansion area 2 for the aerosol. The flow of the supplied gaseous medium M is indicated as an example in the plane of the drawing in FIG. 2. FIG. 2 furthermore shows several arrows which represent the supplied gaseous medium M, which disperses around the flow influencing means 5 and circulates around the flow influencing means 5 such that it finally flows along the rim of the expansion spatial area 2 in which the aerosol cloud released by the aerosol generator 1 disperses centrally. Owing to the design of the flow influencing means 5, it is achieved, as shown in FIG. 2, that the gaseous medium M forms, essentially at the rim of the expansion area 2, a sheath flow m which can be regarded as a quasi-laminar flow in the regions of the rim of the expansion area 2. Although a mixing of the aerosol cloud and the sheath flow of the gaseous medium, which is caused by slight turbulences that are unavoidable in practice, occurs as the two progress through the expansion spatial area 2, it is, however, ensured owing to the deflection and redirection of the supplied gaseous medium M by the flow influencing means 5 that to a considerable extent, the gaseous medium is primarily in the form of a sheath flow m around the aerosol cloud, which moves in an expanding manner away from the aerosol generator 1 in the expansion spatial area 2, just like the sheath flow m of the supplied gaseous medium M.

In the embodiment of the invention shown in FIGS. 1 and 2, the flow influencing means is realised in the form of a cylindrical tube piece 5 which is disposed around the expansion area 2. The aerosol cloud generated by the aerosol generator expands into the cylindrical tube piece 5. As can furthermore be seen from FIGS. 1 and 2, the cylindrical tube piece has a circular cross-section in the shown embodiment, which is both expedient and advantageous. The supplied gaseous medium M impinges upon the outer sheath surface 5a of the tube piece 5. It flows along the outer sheath surface 5a, around the cylindrical tube piece 5, and thereby expands in the direction of the front end 5b of the tube piece 5. Owing to the deflection and redirection of the flow of the gaseous medium M, the gaseous medium M is essentially distributed evenly around the cylindrical tube piece 5 and reaches the front end 5b, which is disposed opposite the aerosol generator 1, so that the gaseous medium flows around the front end 5b of the tube piece 5 and in the rim region of the expansion zone 2 of the aerosol cloud, flows further along the inner surface of the tube piece 5. The desired cylindrical sheath flow m thereby forms around the expansion spatial area 2 for the aerosol. As the sheath flow m and the aerosol cloud progress through the tube piece 5, a continuous but gentle mixing of the gaseous medium and the aerosol cloud occurs since owing to the quasi-laminar nature of the sheath flow m, no strong turbulences occur. As the expanding aerosol cloud progresses, the sheath flow m thereby ensures, however, that virtually no aerosol droplets/particles are deposited on the inner wall surface of the tube piece 5.

As can be seen from FIGS. 1 and 2, in the shown embodiment the tube piece 5 is advantageously integrally formed with a mouthpiece 8 or a connecting piece for a breathing mask, via which the patient inhales the aerosol and the supplied gaseous medium. The design of a connecting piece for a breathing mask is similar to the mouthpiece 8 shown in the figure, and thus an additional description is unnecessary and reference can also be made to FIGS. 1 and 2 as regards the connecting piece for a breathing mask. If there is a supply of ventilation air from a ventilation device, all of the respiratory air is supplied to the patient via the mouthpiece 8/breathing mask. It is achieved by means of the integral design of the tube piece 5 and the mouthpiece 8/connecting piece that a sheath flow m, which prevents the deposition of aerosol droplets/particles, is maintained virtually until entry into the mouth and pharynx of the patient.

In the embodiment of an inhalation therapy device according to the invention as shown in FIGS. 1 and 2, the cylindrical tube piece 5 is disposed in a chamber 6, into which the aerosol generator 1 releases the aerosol. The chamber 6 is surrounded by a section 9 of the housing of the inhalation therapy device, with the housing section 9, just like the cylindrical tube piece 5, having a cylindrical, for example a circular cylindrical, cross-section. This coordination between the chamber 6 and the tube piece 5 is, however, not absolutely necessary in order to achieve the effect explained herein. This is because a gap region 7 is in any case provided between the inner wall 6a of the chamber 6 and the outer sheath surface 5a of the cylindrical tube piece 5, in which the supplied gaseous medium M can disperse.

Since the gap region 7 is terminated in an area 7a that is disposed at a distance from the aerosol generator 1, the expansion of the gaseous medium M occurs in the direction of the end face 5b of the tube piece 5, which is opposite the aerosol generator 1. The termination of the gap region 7 in the area 7a preferably occurs in such a manner that the housing 9 of the inhalation therapy device is integrally formed with the tube piece 5, as is shown in FIGS. 1 and 2 for the explained embodiment.

It can furthermore be seen from FIGS. 1 and 2 with regard to the explained embodiment of the inhalation therapy device according to the invention that the supply means for the gaseous medium M is preferably a cylindrical connecting piece 4, which is provided on the housing 9 of the inhalation therapy device and opens in the direction of the chamber 6. The outlet 4a of the cylindrical connecting piece 4 is thereby arranged so that it is aligned on the tube piece 5 in such a manner that this tube piece 5 has a deflective and redirectional effect on the gaseous medium M.

The position of the outlet 4a and the cylindrical connecting piece 4 is indicated in FIG. 1 by a dashed line. It can be seen from this figure that the cylindrical connecting piece 4 preferably has a circular cylindrical cross-section and is disposed centrally to the cylindrical tube piece 5. The connecting piece 4 can, however, also have a different cross-section, for example an elliptical cross-section, and/or can be disposed eccentrically to the tube piece 5. It is decisive according to the invention that the supply of the gaseous medium M via the supply means 4 occurs in relation to the flow influencing means 5 such that the latter can exert its deflective and redirectional effect on the supplied gaseous medium M and that a sheath flow m is formed around the expansion area 2 for the aerosol.

The supply means 4 of the shown embodiment furthermore comprises a connecting piece 4b for connecting a line, for example a hose. The gaseous medium M, in particular the ventilation air of a ventilation device, is supplied to the inhalation therapy device according to the invention via the hose. Finally, the supply means 4 also permits the supply of air flows generated in another manner, for example also the ambient air inhaled by a patient who is actively breathing, which enters into the supply means 4.

The invention claimed is:

1. An inhalation therapy device comprising:
   an aerosol generating device, designed to generate an aerosol from a liquid containing a medicament and to release said aerosol into an expansion spatial area,
   a liquid storage apparatus, designed to store said liquid and to supply the liquid to said aerosol generating device,
   a cylindrical connecting piece, designed to supply a gaseous medium and
   a cylindrical tube piece, designed to influence the flow of the supplied gaseous medium in such a manner that the gaseous medium forms a sheath flow inside the cylindrical tube piece around the expansion spatial area for the aerosol.

2. An inhalation therapy device comprising:
   an aerosol generating device, designed to generate an aerosol from a liquid containing a medicament and to release said aerosol into an expansion spatial area,
   a liquid storage apparatus, designed to store said liquid and to supply the liquid to said aerosol generating device,
   a cylindrical connecting piece, designed to supply a gaseous medium and
   a cylindrical tube piece arranged around the expansion spatial area such that the supplied gaseous medium impinges upon the outer sheath surface of the tube piece and flows to a front end in the interior of the tube piece such that the gaseous medium forms a sheath flow inside the cylindrical tube piece around the expansion spatial area for the aerosol.

3. An inhalation therapy device according to claim 2, wherein the cylindrical tube piece is disposed in a chamber surrounded by the inhalation therapy device in such a manner that a gap region for the dispersion of the supplied gaseous medium is formed between an outer sheath surface of the cylindrical tube piece and an inner wall surface of said chamber.

4. An inhalation therapy device according to claim 2, wherein the front end of the cylindrical tube piece is disposed in front of the aerosol generating device.

5. An inhalation therapy device according to claim 4, wherein the distance between the front end of the tube piece and the aerosol generating device is smaller than the largest diameter of the tube piece.

6. An inhalation therapy device according to claim 2, wherein the cylindrical tube piece is circular cylindrical.

7. An inhalation therapy device according to claim 2, wherein a mouthpiece or a connecting piece for a breathing mask is provided, which is formed integrally with the cylindrical tube piece.

8. An inhalation therapy device according to claim 3, wherein a housing section of the inhalation therapy device which surrounds the chamber is configured integrally with the cylindrical tube piece.

9. An inhalation therapy device according to claim 2, wherein the cylindrical connecting piece has an outlet which is directed towards the cylindrical tube piece.

10. An inhalation therapy device according to claim 1, wherein the cylindrical tube piece influences the flow of the supplied gaseous medium such that the gaseous medium forms a quasi-laminar sheath flow inside the flow influencing means around the expansion spatial area for the aerosol.

11. An inhalation therapy device according to claim 2, wherein the cylindrical tube piece is arranged around the expansion spatial area such that the gaseous medium forms a quasi-laminar sheath flow inside the cylindrical tube piece around the expansion spatial area for the aerosol.

* * * * *